(12) United States Patent
Guillaume et al.

(10) Patent No.: US 8,143,432 B2
(45) Date of Patent: Mar. 27, 2012

(54) PROCESS FOR REGIOSELECTIVE MONO-TOSYLATION OF DIOLS

(75) Inventors: Michel Joseph Maurice André Guillaume, Berg (BE); Yolande Lydia Lang, Vosselaar (BE)

(73) Assignee: Janssen Pharmaceutica N.V. (BE)

( * ) Notice: Subject to any disclaimer, the term of this patent is extended or adjusted under 35 U.S.C. 154(b) by 318 days.

(21) Appl. No.: 12/515,407

(22) PCT Filed: Nov. 9, 2007

(86) PCT No.: PCT/EP2007/062109
§ 371 (c)(1),
(2), (4) Date: May 18, 2009

(87) PCT Pub. No.: WO2008/058902
PCT Pub. Date: May 22, 2008

(65) Prior Publication Data
US 2010/0016623 A1    Jan. 21, 2010

(30) Foreign Application Priority Data
Nov. 17, 2006    (EP) .................................... 06124292

(51) Int. Cl.
*C07C 303/04*    (2006.01)
(52) U.S. Cl. ......................................................... 558/44
(58) Field of Classification Search ...................... 558/44
See application file for complete search history.

(56) References Cited

FOREIGN PATENT DOCUMENTS
EP    0448413    9/1991
WO    WO 98/09942    3/1998

OTHER PUBLICATIONS

Boons et al., Synlett; No. 12; pp. 913-917 (1993).
David et al., *Tetrahedron* 1985, 41, 643.
Fasoli et al., *J. Mol. Cat. A* 2006, 244, 41.
Hua te al., Tetrahedron Letters; vol. 43; No. 48; pp. 8697-8700 (2002).
Martinelli et al., *J. Am. Chem. Soc.* 2002, 124, 3578.
Martinelli et al., Organic Letters, American Chemical Society; vol. 1; No. 3; pp. 447-450 (1999).
Murata et al., American Chemical Society; vol. 70; No. 6; pp. 2398-2401 (2005).
Seo et al., Journal of Organic Chemistry, vol. 72, No. 2, pp. 666-668, XP002469169 (2006).
Seo et al., "Supporting information" Journal of Organic Chemistry, [Online] XP002469170, American Chemical Society, Washington, DC, US Retrieved from the Internet: URL: http://pubs.acs.org/subscribe/journals/joceah/suppinfo/jo061980u/jo061980usi20061115_074917.pdf > [retrieved on Apr. 4, 2007] p. S5.
Shanzer, A. *Tet. Letters* 1980, 21, 221.
Tinsley, et al., Journal of the American Chemical Society; vol. 127; No. 31; pp. 10818-10819 (2005).
Tinsley, et al., "Supporting Information, Part I" Journal of the American Chemical Society, [Online] Jul. 13, 2005, pp. SI-SI8, XP002428306 American Chemical Society, Washington, DC, US, retrieved from the internet: URL: http://pubs.acs.org/subscribe/journals/jacsat/suppinfo/ja0519861/ja0519861si20050610_013126.pdf.
Zarbin et al., Tetrahedron Letters; vol. 44; No. 36; pp. 6849-6851 (2003).

*Primary Examiner* — Joseph Kosack
(74) *Attorney, Agent, or Firm* — Yuriy P. Stercho

(57) ABSTRACT

The present invention concerns the use of dibutyl tin oxide for regioselective catalytic diol mono-tosylation at a concentration lower than 2 mol %. The present invention also concerns the use of a generic acetal compound of Formula (Ic) in a catalytic process for regioselective diol mono-tosylation, wherein Y is selected from the group of $C_{1-6}$alkyl, phenyl and benzyl. The concentration of the generic acetal compound of Formula (Ic) is less than about 2 mol %, preferably ranges between about 2 mol % and about 0.0005 mol %, preferably ranges between about 0.1 mol % and about 0.005 mol %.

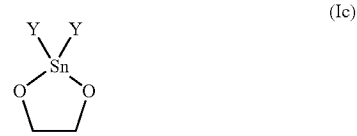

(Ic)

3 Claims, No Drawings

PROCESS FOR REGIOSELECTIVE MONO-TOSYLATION OF DIOLS

CROSS REFERENCE TO RELATED APPLICATIONS

This application is the national stage of PCT Application No. PCT/EP2007/062109, filed Nov. 9, 2007, which claims priority from European Patent Application No. 06124292.1, filed Nov. 17, 2006, the entire disclosures of which are hereby incorporated in their entirety.

INTRODUCTION

It is well known in the art that the concentration of impurities, in particular metal impurities in the production of API's (active pharmaceutical intermediates) should be as low as possible to avoid labour-intensive and expensive purification methods, such as e.g. recrystallisation. This restriction poses severe limitations to the use of reagents in metal-catalysed synthesis processes of API's and it is generally desired to use only to a limited extent reagents and intermediates based on metals, in particular heavy metals. One such reaction that is commonly used, is the regioselective diol mono-tosylation reaction. Such a reaction may be performed without the use of a metal-containing catalyst, however, in a number of instances, low conversion and/or selectivity (defined as the ratio of mono- to di-tosylated product), is commonly observed.

The use of dibutyl tin oxide 1 ($Bu_2SnO$) is well known for the regioselective derivatization of vicinal diols 2. Since Shanzer's original paper (Shanzer, A. *Tet. Letters* 1980, 21, 221), the stoechiometric process has been widely applied in sugar chemistry (David, S.; Hanessian, S. *Tetrahedron* 1985, 41, 643 and Walkup, R. E.; Vernon, N. M. Wingard, R. E., Jr. Patent Application EP 448413 A1, 1991). The reaction can be generalized to functionalize other diols as well (Boons, G.-J.; Castle, G. H.; Clase, A.; Grice, P.; Ley, S. V.; Pinel, C. Synlett 1993, 913). Unfortunately, since the reaction is stoechiometric, it requires a high amount of dibutyl tin oxide, which further needs to be separated from the reaction mixture.

The catalytic process, described in 1999 by Martinelli and co-workers (Martinelli, M. J.; Nayyar, N. K.; Moher, E. D.; Dhokte, U. P.; Pawlak, J. M.; Vaidyanathan, R. *Org. Letters* 1999, 1, 447) allows the selective mono-tosylation of a diol with only 2 mol % of $Bu_2SnO$ in the presence of a classical base like triethylamine ($Et_3N$). In a more recent paper (Martinelli, M. J.; Vaidyanathan, R.; Pawlak, J. M.; Nayyar, N. K.; Dhokte, U. P.; Doecke, C. W.; Zollars, L. M. H.; Moher, E. D.; Khau, V. V.; Komšmrlj, B. *J. Am. Chem. Soc.* 2002, 124, 3578), the mechanistic aspects of the reaction were detailed (Scheme 1). The intermediate formation of the corresponding tin acetal 3 was postulated, which is also in accordance with the reactivity of tin acetals isolated in the stoechiometric process.

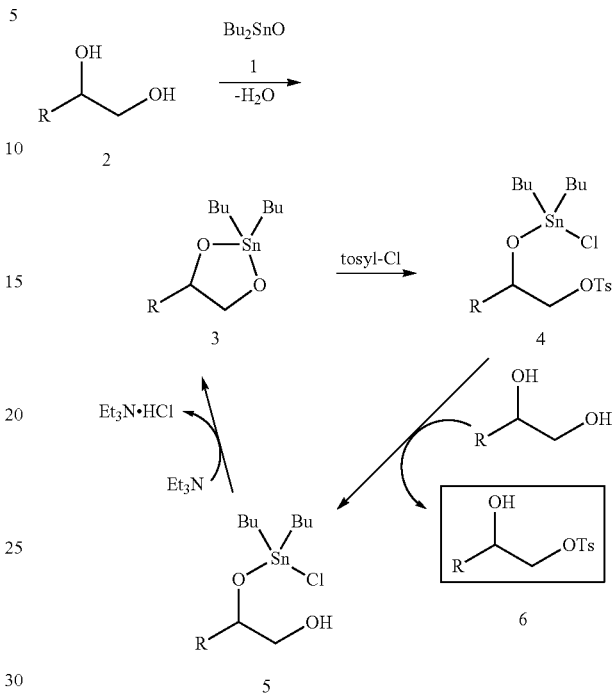

Scheme 1 Catalytic process of $Bu_2SnO$-catalyzed diol mono-tosylation. For simplicity, the dimeric structurres indicated in Martinelli's paper were omitted.

Tin acetal intermediates like 3 are considered to be more reactive than 1 and to give more reproducible results. In a recent paper, Fasoli et al. (Fasoli, E. Caligiuri, A.; Servi, S.; Tessaro, D. *J. Mol. Cat. A* 2006, 244, 41) described mono-benzoylation of a diol with catalytic Sn acetal derived either from the reacting diol itself, or from alcohols like methanol or isopropanol.

The inventors have now found that in the above catalytic process of regioselective mono-tosylation of vicinal diols, the amount of dibutyl tin oxide 1 can surprisingly be reduced from the disclosed 2 mol % to 0.1 mol %, without any loss of conversion and selectivity.

The inventors have also found that a generic Sn-acetal, advantageously independent of the reacting diol itself, and advantageously in a solid form, can be used in the above catalytic process of regioselective mono-tosylation of vicinal diols, preferably at concentrations well below 2 mol %, in particular below 0.1 mol %, and even down to 0.001 mol % to yield a very high conversion and selectivity. The process is applicable on different commercial diol substrates and has the major advantage that only trace amounts of Sn (lower ppm-range) remain in the API.

DESCRIPTION OF THE INVENTION

The present invention concerns the use of dibutyl tin oxide for regioselective catalytic diol mono-tosylation at a concentration lower than 2 mol %, preferably in the range between 2 mol % and about 0.05 mol %, inclusive, in particular about 0.1 mol %.

The present invention also concern a process for the regioselective catalytic diol mono-tosylation, comprising a step wherein a compound comprising a diol moiety of Formula (Ia) is tosylated into a compound comprising a tosylated diol moiety of Formula (Ib) using less than 2 mol % of $Y_2SnO$,

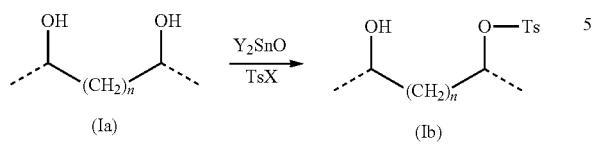

wherein

Y is selected from the group of $C_{1-6}$alkyl, phenyl and benzyl;

X is selected from the group of Cl, Br, and OTs; and n is an integer equal to 1 or 2.

In one embodiment, the concentration of $Y_2SnO$ ranges between 2 mol % and about 0.05 mol %, inclusive. In another embodiment, the concentration of $Y_2SnO$ is about 0.1 mol %.

The present invention also concerns the use of a generic acetal compound of Formula (Ic) in a catalytic process for regioselective diol mono-tosylation,

wherein Y is selected from the group of $C_{1-6}$alkyl, phenyl and benzyl.

The generic acetal compound of Formula (Ic) can be made according to preparation methods well-known in the art, for example, according to methods disclosed in EP 448413 B1 (Noramco Inc), which are herein included by reference. The acetal compound of Formula (Ic) may also be formed in situ when compounds of Formula (Ia) are tosylated. However, it is preferred that the acetal compound of Formula (Ic) is different from the acetal compound formed in the regioselective diol mono-tosylation reaction.

The present invention also concerns the use of a generic acetal compound of Formula (Ic) in a catalytic process for regioselective diol mono-tosylation, wherein Y is selected from the group of $C_{1-6}$alkyl, phenyl and benzyl, wherein the concentration of the compound of Formula (Ic) is less than about 2 mol %, preferably ranges between about 2 mol % and about 0.0005 mol %, preferably ranges between about 0.1 mol % and about 0.005 mol %.

The present invention also concern a process for the catalytic regioselective diol mono-tosylation, wherein a compound comprising a diol moiety of Formula (Ia) is tosylated into a compound comprising a tosylated diol moiety of Formula (Ib) using a generic acetal compound of Formula (Ic), wherein

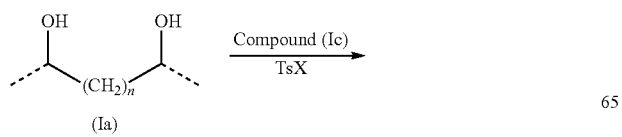

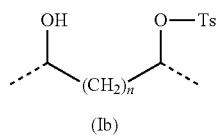

Y is selected from the group of $C_{1-6}$alkyl, phenyl and benzyl;

X is selected from the group of Cl, Br, and OTs; and n is an integer equal to 1 or 2.

According to one embodiment, the concentration of the generic acetal compound of Formula (Ic) is less than about 2 mol %, preferably ranges between about 2 mol % and about 0.0005 mol %, preferably ranges between about 0.1 mol % and about 0.005 mol %.

According to another embodiment, Y is butyl. According to another embodiment, the generic acetal compound of Formula (Ic) is 2,2-dibutyl-[1,3,2]dioxastannolane, which is a commercially available raw material.

Within the framework of this application, tosyl is an abbreviation for p-toluenesulfonate. It is the conjugate base of the strong acid, p-toluenesulfonic acid. The tosyl group, like other sulfonates, is a highly reactive leaving group. The process of introducing a tosyl-group into a molecule, is called mono-tosylation.

Within the framework of this application, a diol moiety is a moiety comprising at least two hydroxy groups, separated by at least 2 and at most 3 carbon atoms.

Within the framework of this application, "regioselective" means that the reaction takes place only at the primary alcohol.

Results and Discussion

A. Preparation of acetic acid 8-fluoro-11-[2-hydroxy-3-(toluene-4-sulfonyloxy)-propyl]-10,11-dihydro-5H-dibenzo[a,d]cyclohepten-10-yl ester (Compound 6a)

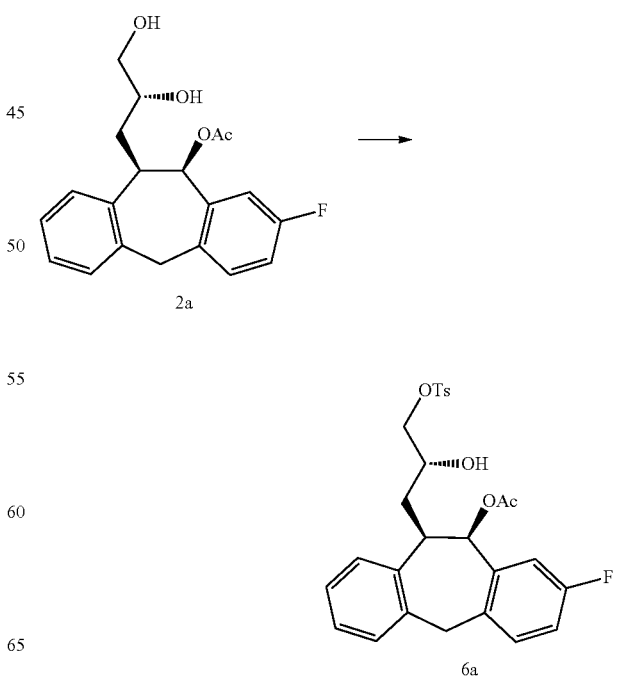

Compound 2a was tosylated using a variety of conditions. In short (lab procedure (0.1 mol scale): To compound 2a (34.4 g, 0.1 mol) in toluene (1.2 L/mol) compound 1 (various amounts) is added at 25° C. The mixture is stirred during 1 hour. Diisopropyl ethylamine, triethylamine or pyridine (various amounts) is added and the reaction mixture is stirred during 5 min. Tosyl chloride (various amounts) is added and the reaction mixture is stirred at that temperature during 16 hours. Hydrochloric acid 1N (150 ml) is added and the mixture is stirred vigorously. pH of the aqueous phase is 1 to 2; the organic phase is filtered over sodium sulfate and used further in the next step.

Example 17 was further conducted on a pilot plant scale (35 mol scale): To compound 2a in toluene (34 L) compound 1 (9 g, 0.25 g/mol) is added and the mixture is stirred at 25° C. during 1 hour. N,N-diisopropyl ethyl amine (5.0 kg, 38.4 mol) is added, followed by tosyl chloride (7.0 kg, 36.8 mol). After stirring the reaction mixture at 25° C. during 16 hours, HCl 1N (1.35 eq.) in water is added. The pH of the aqueous layer is 1 to 2. The organic layer is dried over $Na_2SO_4$ (3.5 kg) and used as such in the next step. The estimated yield was 80%.

The results are shown in Table 1. Compounds according to Formula 2a and 6a are known from Mao, Hua; Koukni, Mohamed; Kozlecki, Tomasz; Compernolle, Frans; Hoornaert, Georges J. Diastereoselective synthesis of trans-fused tetrahydropyran derivatives of 5H-dibenzo[a,d]cycloheptene. Tetrahedron Letters (2002), 43(48), 8697-8700. From the Table 1 can be seen that the amount of $Bu_2SnO$ in the catalyzed mono-tosylation reaction could be lowered down to as low as 0.1 mol %. Unlike Martinelli (Martinelli, M. J.; Nayyar, N. K.; Moher, E. D.; Dhokte, U. P.; Pawlak, J. M.; Vaidyanathan, R. Org. Letters 1999, 1, 447.), some unidentified impurities were formed when $Et_3N$ was used, while diisopropyl ethyl amine (i-$Pr_2$NEt, Hünig's base) gave cleaner reaction. We acknowledge however that this latter point might strongly depend on the substrate used.

TABLE 1

| Ex. | $Bu_2SnO$ (mol %) | TsCl (eq.) | pyridine (eq.) | $Et_3N$ (eq.) | i-$Pr_2$NEt (eq.) | Conversion (%) | Selectivity* (mono:di) |
|---|---|---|---|---|---|---|---|
| 1 | 0 | 1.5 | 10 | — | — | 92 | 86:14 |
| 2 | 10 | 1.5 | — | 1.5 | — | >99 | 90:10 |
| 3 | 5 | 1.05 | — | 1.05 | — | >99 | 96:4 |
| 4 | 2 | 1.05 | — | 1.05 | — | >99 | 96:4 |
| 5 | 2 | 1.1 | — | 1.1 | — | >99 | 94:6 |
| 6 | 1 | 1.05 | — | 1.05 | — | >99 | 94:6 |
| 7 | 1 | 1 | — | 1.05 | — | 87 | 92:8 |
| 8 | 0 | 1.05 | — | — | 1.2 | Only 60% conversion after 4 days | |
| 9 | 1 | 1.1 | — | — | 1.15 | 93 | 91:9 |
| 10 | 0.5 | 1 | — | — | 1.05 | 97 | 98:2 |
| 11 | 0.5 | 1.1 | — | — | 1.2 | 95 | >99:1 |
| 12 | 0.5 | 1.05 | — | — | 1.2 | >99 | >99:1 |
| 13 | 0.1 | 1.05 | — | — | 1.2 | 97 | 96:4 |
| 14 | 0.05 | 1.05 | — | — | 1.2 | Only 50% conversion after 16 hours at r.t. | |

*HPLC, area %. Samples were analyzed after 1 hour reaction, unless stated otherwise. No favourable evolution is observed after 3, 6 or 24 hours.

B. Preparation of 2,2-dibutyl[1,3,2]dioxastannolane

The tin acetal 2,2-dibutyl[1,3,2]dioxastannolane was prepared from $Bu_2SnO$ and ethylene glycol according to the following procedure (scheme 3)

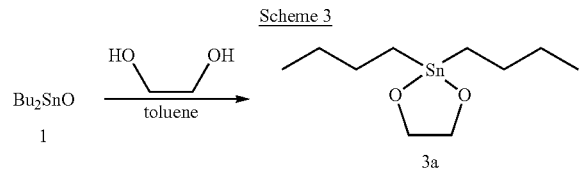

Scheme 3

The following experiment was only performed at lab scale (0.1 mol). Compound 1 (24.9 g, 0.1 mol) is dissolved in toluene (100 ml, 1 L/mol). Ethylene glycol (28 ml, 5 eq.) is added at 25° C. Water is removed azeotropically at 110-114° C. and the reaction mixture is stirred at that temperature during 5 hours. After gradual cooling (110° C.→20° C. over 12 hours), the precipitate 3a is filtered, washed and dried at 40° C. under vacuum. Yield: 27.4 g (93%). Compound 3b is used as such for further experiments. For analytical purposes, a 10 g sample is recrystallised in toluene (40 ml, 4 ml/g) with gradual cooling (110° C.→20° C. over 10 hours). Anal. Calcd. for $C_{10}H_{22}O_2Sn$: C, 41.00; H, 7.57. Found: C, 40.68; H, 7.70.

NMR $^1$H-CDCl$_3$: 0.9 (t, 6H), 1.3 (m, 4H), 1.4 (m, 4H), 1.63 (m, 4H), 3.62 (s, 4H)

C. Regioselective diol mono-tosylation Using the Generic Acetal Compound 3a

The generic acetal compound 3a was used to perform the mono-tosylation reaction according Scheme 2 for a series of compounds. In short, a mixture of the corresponding diol, stannylene acetal 3a, i$Pr_2$NEt and TsCl in various amounts was stirred at room temperature for 16 hours. Hydrochloric acid 1N (1.5 eq.) was added and the mixture was stirred vigorously. The organic phase was filtered over sodium sulfate and used further as such in the next step.

The results are shown in Table 2. From the Table 2 can be seen that the amount of compound 3a in the catalyzed mono-tosylation reaction could be lowered down to as low as 0.001 mol %. This presents a major improvement over the prior art preparation methods and allows for the production of API's with very low Sn concentrations.

TABLE 2

| Nr. | Substrate | Bu₂SnO (mol %) 0.1 Conversion (%) Selectivity (mono:di) | Bu₂Sn(OCH₂CH₂O) cyclic (mol %) | | | | |
|---|---|---|---|---|---|---|---|
| | | 0.1 | 0.1 | 0.05 | 0.01 | 0.005 | 0.001 | 0.0005 |
| 1 | (stereochemistry-defined tricyclic substrate with OH, OH, OAc, F groups) | 97<br>96:4 | 97<br>96:4 | 97<br>>99:1 | — | 84<br>>99:1 | — | — |
| 2 | 3-(2-methoxyphenoxy)propane-1,2-diol | 96<br>95:5 | 97<br>97:3 | 97<br>97:3 | 92<br>98:2 | 94<br>95:5 | 85<br>95:5 | 81<br>89:11 |
| 3 | 1-phenyl-1,2-ethanediol | 95<br>99:1 | 97<br>>99:1 | 98<br>>99:1 | 92<br>99:1 | 87<br>99:1 | 70<br>96:4 | — |
| 4 | 3-phenoxypropane-1,2-diol | 95<br>99:1 | 95<br>99:1 | 95<br>98:2 | 96<br>95:5 | 92<br>93:7 | 63<br>70:30 | — |
| 5* | pentane-1,2-diol | 93 | 88 | 88 | 84 | 83 | 0 | — |
| 6* | but-3-ene-1,2-diol | 85 | 86 | 86 | 68 | — | — | — |

Substrates 1 to 4: % conversion and selectivity is based on HPLC area %.

Substrates 5 and 6: % conversion and selectivity is based on GC area %.

*The GC chromatogram didn't show any ditosylation or starting material, analysis with HPLC showed some ditosylation.

The invention claimed is:

1. Process for the catalytic mono-tosylation of a diol, comprising a step wherein a compound comprising a diol moiety of Formula (Ia) is tosylated into a compound comprising a tosylated diol moiety of Formula (Ib) using a compound of Formula (Ic)

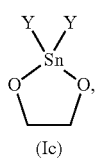
(Ic)

wherein Y is selected from the group of $C_{1-6}$alkyl, phenyl, and benzyl, in a concentration between 2 mol % and 0.0005 mol %,

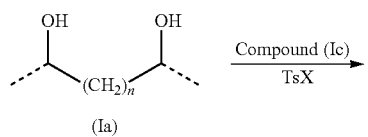
(Ia)

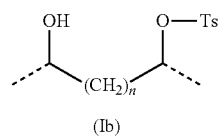
(Ib)

wherein

X is selected from the group of Cl, Br, and OTs; and n is an integer equal to 0 or 1.

2. The process as claimed in claim 1 wherein the concentration of the compound of Formula (Ic) is between 0.1 mol % and 0.005 mol %.

3. The process as claimed in claim 2 wherein the compound of Formula (Ic) is 2,2-dibutyl-[1,3,2]dioxastannolane.

* * * * *